United States Patent
Hilman et al.

(10) Patent No.: US 6,787,531 B1
(45) Date of Patent: *Sep. 7, 2004

(54) PHARMACEUTICAL COMPOSITION FOR USE AS A CONTRACEPTIVE

(75) Inventors: Juergen Hilman, Berlin (DE); Wolfgang Heil, Berlin (DE); Ralph Lipp, Berlin (DE); Renate Heithecker, Berlin (DE); Michael Huempel, Berlin (DE); Johannes W. Tack, Berlin (DE)

(73) Assignee: Schering AG, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/654,227

(22) Filed: Aug. 31, 2000

Related U.S. Application Data

(60) Provisional application No. 60/240,953, filed on Aug. 31, 1999.

(51) Int. Cl.[7] .............................................. A61K 31/56
(52) U.S. Cl. ....................................... 514/171; 514/178
(58) Field of Search .................................. 514/171, 178, 514/181

(56) References Cited

U.S. PATENT DOCUMENTS

| | | |
|---|---|---|
| 4,129,564 A | 12/1978 | Wiechert et al. |
| 4,217,347 A | 8/1980 | Horovitz et al. |

(List continued on next page.)

FOREIGN PATENT DOCUMENTS

| | | |
|---|---|---|
| CA | 2188907 | 2/2001 |
| DE | 3022337 A1 | 1/1982 |
| DE | 30 22 337 | 10/1989 |
| DE | 30 51 166 | 10/1990 |
| EP | 0 148 724 | 6/1988 |
| EP | 0 253 607 | 4/1992 |
| EP | 0 398 460 | 2/1997 |
| EP | 0 770 388 | 3/1998 |
| GB | 2192542 | 1/1988 |
| WO | 94/04157 | 3/1994 |

(List continued on next page.)

OTHER PUBLICATIONS

An Invitation (one page) for and 21 slides shown in an oral presentation held on Feb. 17, 1988 in Berlin, Germany, entitled "Studies on pH–dependent Isomerization of Pregnene–17,21–Carbolactones." by Johannes W. Tack. (Original in German with English translation.)

Sattar, et al., J.Clin.Endocrin.&Metab., vol. 82, No. 8, 1483–2491 (1997).

(List continued on next page.)

*Primary Examiner*—San Ming R. Hui
(74) *Attorney, Agent, or Firm*—Millen, White, Zelano, Branigan, P.C.

(57) ABSTRACT

A pharmaceutical composition comprises, as a first active agent, 6β,7β;15β,16β-dimethylene-3-oxo-17α-pregn-4-ene-21,17-carbolactone (drospirenone) in an amount corresponding to a daily dosage, on administration of the composition, of from about 2 mg to about 4 mg, and, as a second active agent, 17α-ethinylestradiol (ethinylestradiol) in an amount corresponding to a daily dosage of from about 0.01 mg to about 0.05 mg, together with one or more pharmaceutically acceptable carriers or excipients.

In a specific embodiment, the composition consists of a number of separately packaged and individually removable daily dosage units placed in a packaging unit and intended for oral administration for a period of at least 21 consecutive days, wherein said daily dosage units comprises the combination of drospirenone and ethinylestradiol. The composition may further comprise 7 or less daily dosage units containing no active agent or containing ethinylestradiol alone.

52 Claims, 5 Drawing Sheets

U.S. PATENT DOCUMENTS

| | | | |
|---|---|---|---|
| 4,621,079 A | | 11/1986 | Lachnit-Fixson et al. |
| 5,001,113 A | | 3/1991 | Williams et al. |
| 5,534,270 A | * | 7/1996 | De Castro .................. 424/490 |
| 5,569,652 A | | 10/1996 | Beier et al. |
| 5,583,129 A | | 12/1996 | Spona et al. |
| 5,756,490 A | | 5/1998 | Lachnit et al. |
| 5,824,667 A | | 10/1998 | Spona et al. |
| 5,827,843 A | | 10/1998 | Koninckx |
| 5,922,349 A | * | 7/1999 | Elliesen et al. |
| 6,083,528 A | | 7/2000 | Elliesen et al. |
| 6,121,465 A | | 9/2000 | Mohr et al. |
| RE37,564 E | | 2/2002 | Spona et al. |

FOREIGN PATENT DOCUMENTS

| | | | |
|---|---|---|---|
| WO | WO 95/07081 A1 | | 3/1995 |
| WO | 95/17194 | | 6/1995 |
| WO | 95/26730 | | 10/1995 |
| WO | 97/01342 | | 1/1997 |
| WO | WO 97/10827 A1 | | 3/1997 |
| WO | WO 97/11680 A2 | | 4/1997 |
| WO | WO 98/04267 | * | 2/1998 |
| WO | 98/04267 | | 2/1998 |
| WO | WO 98/04269 | * | 2/1998 |
| WO | 98/04269 | | 2/1998 |
| WO | 98/06738 | | 2/1998 |
| WO | 98/24801 | | 6/1998 |
| WO | WO 98/27929 A2 | | 7/1998 |

OTHER PUBLICATIONS

Elstein et al., "Advances in Oral Hormonal Contraception," *Zentralbl Gynakol* 117 (1995) 559–565.

Oelkers et al., "Effects of the new progestogen and antimineralocortoid dihydrospirorenone," *Acta Endocrinologica* 1992: 126 Suppl. 4, p. 71.

Oelkers et al., (1991) "Dihydrospirorenone, a New Progestogen with Antimineralocortcoid Activity: Effects on Ovulation, Electrolyte Excretion, and the Renin–Aldosterone System in Normal Women" *Journal of Clinical Endocrinology and Metabolism,* vol. 73, No. 4, 837–842.

Oelkers, "Effects of oral contraceptives on the renin—aldosterone system: overview and report on a new natriuretic progestogen," *Advances in Contraception,* 7 Suppl. 3 (1991) 195–206.

Kincl et al., "Increasing Oral Bioavailability of Progesterone by Formulation," *Journal of Steroid Biochemistry,* 1978, vol. 9, pp. 83–84.

Whitehead et al., "Absorption and metabolism of oral progesterone," *British Medical Journal,* Mar. 22, 1980, pp. 825–827.

Maxson et al., "Bioavailability of oral micronized progesterone," *Fertility and Sterility,* vol. 44, No. 5, Nov. 1985, pp. 622–626.

Chakmakjian et al., "Bloavailability of Progesterone with Different Modes of Administration," *The Journal of Reproductive Medicine,* vol. 32, No. 6, Jun. 1987, pp. 443–448.

Hargrove et al., "Absorption of oral progesterone is influenced by vehicle and particle size," *Am J Obstet Gynecol,* vol. 161, No. 4, Oct. 1989, pp. 948–951.

Kohno et al., "Pharmacokinetics and Bioavailability of Diltlazem (CRD–401) in Dog," *Arzneim.–forsch./Drug Res.,* 27 (II), No. 7 (1977), pp. 1424–1428.

Nürnberg, "Manufacturing and Properties of Pharmaceutical Spray–Dried Products," *Acta Pharmaceutica Hungarica* 48. 19–35. 1978 (and English translation).

Lehto et al., "The Effect of pH on the in–vitro Dissolution of Three Second–generation Sulphonylurea Preparations: Mechanism of Antacid–sulphonylura Interaction," *J. Pharm. Pharmacol.* 1996, 48: 899–901.

Clarke et al., "Factors Influencing Comparative Bioavailability of Spironolactone Tablets," *Journal of Pharmaceutical Sciences,* vol. 66, No. 10, Oct. 1977, pp. 1429–1432.

"Bioavailability and Bioequivalence," *Biopharmacy,* Chapter 7 (English translation part ½ of p. 202, Chapter 7).

Berger et al., (1992) "Influence of Different Progestogens on Blood Pressure of Non–Anaesthetized Mate Spontaneously Hypertensive Rats" *Contraception* 46:83–97.

Skouby, (2000) "The rationale for a wider range of progestogens" *Climacteric,* vol. 3, (Suppl. 2): 14–20.

Norman et al., (2000) "Drospirenone"*Drugs of the Future* 2000, 25(12): 1247–1256.

R. Krattenmacher, (2000) "Drospirenone: pharmacology and pharmacokinetics of a unique progestogen" *Contraception* 62, 29–38.

Fuhrmann et al., (1996) "The Novel Progestin Drospirenone and its Natural Counterpart Progesterone: Biochemical Profile and Antiandrogenic Potential" *Contraception,* 54: 243–251.

Parsey et al., (2000) "An Open–Label, Multicenter Study to Evaluate Yasmin, a Low–Dose Combination Oral Contraceptive Containing Drospirenone, a New Progestogen" *Contraception,* 61: 105–111.

Krause et al., "Isolation and Identification of Spirorenone Metabolites from the Monkey (Macaca Fasclcularis)," *Steroids,* vol. 40, No. 1, Jul. 1982, pp. 81–90.

Krause et al., "Determination of Plasma Levels of Spirorenone, a New Aldosterone Antagonist, and One of its Metabolites by High–Performance Liquid Chromatography," *Journal of Chromatography,* 230 (1982) 37–45.

"Spirorenone," *Drugs of the Future,* vol. 10, No. 6, 1985, pp. 475–481.

Wilson et al., (1984) "A prospective controlled study of the effect on blood pressure of contraceptive preparations containing different types and dosages of progestogen" *Brit. J. Ostet Gynecol*91, 1254–1260.

Nichols et al., (1993) "Effect of four combined oral contraceptives on blood pressure in the pill–free interval" *Contraception* 47, 367–376 (1993).

Oelkers et al., (1974) "Effects of Progesterone and Four Synthetic Progestagens on Sodium balance and the Renin–Aldosterone System in Man" *J. Clin. Endocrinol Metab* 39, 882–890.

Rylance et al., "Natural progesterone and antihypertensive action," *British Medical Journal,* vol. 290, Jan. 5, 1985, p. 13–14.

Luotola, "Blood Pressure and Hemodynamics in Postmenopausal Women During Estradiol–17β Substitution," *Annals of Clinical Research,* vol. 15, Suppl. 38 1983.

Mashchak, et al., "Estrogen Replacement Therapy and Hypertension," *The Journal of Reproductive Medicine,* vol. 30, No. 10 (Supp)/Oct. 1985, p. 805–810.

Rajkumar et al., "Hormonal Therapy Increases Arterial Compliance in Postmenopausal Women," *JACC,* vol. 30, No. 2, Aug. 1997:350–6.

Hayward et al., "Effect of hormone replacement therapy on non–invasive cardiovascular haemodynamics," *Journal of Hypertension,* 1997, vol. 15, No. 9, p. 987–993.

Mercuro et al., "Estradiol–17β Reduced Blood Pressure and Restores the Normal Amplitude of the Circadian Blood Pressure Rhythm in Postmenopausal Hypertension," *American Journal of Hypertension,* vol. 11, No. 8, Part 1, pp. 909–913.

Hayward et al., "Effect of Combination Hormone Replacement Therapy on Ambulatory Blood Pressure and Arterial Stiffness in Diabetic Postmenopausal Women," *American Journal of Hypertension,* Jul. 2001, vol. 14, No. 7, Part 1, pp. 699–703.

Wren et al., "The effect of type and dose of oestrogen on the blood pressure of post–menopausal women," *Maturitas,* 5 (1983) 135–142.

Oelkers, "Reply to Letter to the Editor," *Gynecol Endocrinol,* 2000, 14:476–478.

Seely et al., "Estradiol With or Without Progesterone and Ambulatory Blood Pressure in Postmenopausal Women," *The American Heart Association, Inc.,* May 1999, 1190–1194.

Mercuro et al., "Effects of Acute Administration of Transdermal Estrogen on Postmenopausal Women with Systemic Hypertension," *The American Journal of Cardiology,* vol. 80, Sep. 1, 1997, 652–655.

"Effects of Estrogen or Estrogen/Progestin Regimens on Heart Disease Risk Factors in Postmenopausal Women," *JAMA,* Jan. 18, 1995, vol. 273, No. 3, 199–208.

Pripp et al., "A randomized trial o effects of hormone replacement therapy on ambulatory blood pressure and lipoprotein levels in women with coronary artery disease," *Journal of Hypertension,* 1999, vol. 17, No. 10, 1379–1386.

Manhem et al., "Transdermal oestrogen reduces daytime blood pressure in hypertensive women," *Journal of Human Hypertension,* (1998) 12, 323–327.

Ittersum et al., "Ambulatory–Not Office–Blood Pressure Decline During Hormone Replacement Therapy in Healthy Postmenopausal Women," *American Journal of Hypertension,* 1998, vol. 11, No. 10, part 1, 1147–1152.

Carara et al., "*Abstracts* Thirtieth Annual Meeting American College of Clinical Pharmacology Sep. 23–25, 2001, Vienna, Virgina," J Clin Pharmacol, 2001; 41:1014–1033.

Epstein, "Aldosterone and the hypertensive kidney: Its emerging role as a mediator of progressive renal dysfunction: a paradigm shift," *Journal of Hypertension,* 2001, vol. 19, No. 5, 829–834.

Duprez et al., "Aldosterone and Vascular Damage," *Current Hypertension Reports,* 2000, 2:327–334.

Pitt et al., "The Effect of Sprionolactone on Morbidity and Mortality in Patients with Severe Heart Failure," *The New England Journal of Medicine,* vol. 341, No. 10, Sep. 2, 1999, 709–717.

Farquharson et al., "Spironolactone Increases Nitric Oxide Bioactivity, Improves Endothelial Vasodilator Dysfunction, and Suppresses Vascular Angiotensin I/Angiotensin II Conversion in Patients with Chronic Heart Failure," *Circulation,* Feb. 15, 2000, 594–597.

MacFadyen et al., "Aldosterone blockade reduces vascular collagen turnover, improves heart rate variability and reduces early morning rise in heart rate in heart failure patients," *Cardiovascular Research,* 35 (1997) 30–34.

Chrysostomou et al., "Spironolactone in Addition to ACE Inhibition to Reduce Proteinuria in Patients with Chronic Renal Disease," *N Engl J Med,* vol. 345, No. 12, Sep. 20, 2001, 925–926.

Ellman Declaration with Exhibits A–M.

Prosecution History of Corresponding International Application No. PCT/IB00/01213 at EPO.

Casper et al., "Estrogen and Interrupted Progestin: A New Concept for Menopausal Hormone Replacement Therapy," *American Journal of Obstet Gynecol,* vol. 168, No. 4, pp. 1188–1196.

Lignières, "Oral Micronized Progesterone," *Clinical Therapeutics,* vol. 21, No. 1, 1999, pp. 41–60.

Nickisch et al., "Acid–Catalyzed Rearrangements of 15β, 16β–methylene–17α–pregnene–21,17– carbolactone Derivatives," *Tetrahedron Letters,* vol. 27, No. 45, 1986, pp. 5463–5466.

Translation of Cite No. C4.

Shah et al., "Preformulation Study of Etoposide: Identification of Physicochemical Characteristics Responsible for the Low and Erratic Oral Bioavailability of Etoposide," *Pharmaceutical Research,* vol. 6, May 1999, pp. 408–412.

Montel et al., "Development of a New Tablet Formulation of Theophylline: In Vitro and In Vivo Studies," *Drug Development and Industrial Pharmacy,* vol. 9, No. 3, 1983, pp. 399–420.

Arias et al., "Dissolution Properties and In Vivo Behaviour of Triamterene in Solid Dispersions With Polyethylene Glycols," *Pharm–Acta–Helv,* vol. 71, No. 4, 1996, pp. 229–235.

Berlin et al., "Phase I and Pharmacokinetic Study of a Micronized Formulation of Carboxyamidotriazole, A Calcium Signat Transduction Inhibitor: Toxicity, Bioavailability and the Effect of Food," *Clinical Cancer Research,* Jan. 2002, vol. 8, No. 1, pp. 86–94.

Carlson et al., "Efficacy and Safety of Reformulated, Micronized Glyburide Tablets in Patients With Non–Insulin–Dependent Diabetes Mellitus: A Multicenter, Double–Blind, Randomized Trial," *Clinical Therapeutics,* 1993, vol. 15, No. 5, pp. 788–796.

Duclos et al., "About A Pharmacokinetic Study of Progesterone in Comelts," *Eur–J–Drug–Metab–Pharmacokinet,* vol. 15, No. 2, Suppl., Abstr. 226, 1990.

Fell et al., "Bioavailability of Griseofulvin From a Novel Capsule Formulation," *The Journal of Pharmacy and Pharmacology,* 1978, vol. 30, No. 8, pp. 479–482.

Hartmann et al., "Comparison of Galenic Formulations of Orlistate (Tetrahydrollpstatin). A Pharmacological Approach," *Drug Investigation,* 1993, vol./Iss/p. 5/1 (44–50).

Kohno et al., "Pharmacokinetics And Bioavailability of Diltiazem (CRD–401) In Dog," *Arzneimittel–Forschung,* 1977, vol. 27, No. 7, pp. 1424–1428.

Hsiao et al., "Method for Preparing An Oral Formulation Containing Acid–Sensitive Drugs," *Standard Chem. & Pharm. Co., Ltd.*

Klokkers et al., "Stabilization of Acid Sensitive Benzimidazoles with Amino Acid/Cyclodextrin Combinations."

Bruzzese et al., "Action of Gastric and Intestinal Simulated Juice on Mepartricin Stability in Solid and Solubilized Form," *Il Farmaco–Ed. Pr.,* vol. 32, No. 8, pp. 422–428.

Anderson et al., "Pharmacokinetics and Bioavailability of Omeprazole After Single and Repeated Oral Administration in Healthy Subjects," *Br. J. Clin. Pharmac.,* 1990, vol. 29, pp. 557–563.

Bozdag et al., "Formulation and Stability Evaluation of Enteric–Coated Omeprazole Formulations," *S.T.P. Pharma Sciences,* vol. 9, No. 4, 1999, pp. 321–327.

English language abstract of DE 30 22 337.

English language abstract of DE 30 51 166.
English language abstract of EP 0 398 460.
English language abstract of EP 0 148 724.
Oelkers, W. et al., "Effects of a new oral contaceptive containing an antimineralocortisoid progestogen, drospirenone, on the renin–aldosterone system, body weight, blood pressure, glucose tolerance, and lipid metabolism", *JCE & M*, 1995, vol. 80, No. 6.

Oelkers, W., "Effects f estrogens and progestogens on the renin–aldosteron system and blood pressure", *Steroids*, 1996, vol. 61, Apr.

Muhn Peter, et al, "Drospirenone: A novel progestogen with antimineralocorticoid and antiandrogenic activity", 1995.

* cited by examiner

PHARMACEUTICAL COMPOSITION FOR USE AS A CONTRACEPTIVE

This application claims the benefit of the filing date of U.S. Provisional Application Serial No. 60/240,953 filed Aug. 31, 1999.

FIELD OF THE INVENTION

The present invention relates to a pharmaceutical composition comprising drospirenone and ethinylestradiol, a method of providing dissolution of drospirenone, methods of inhibiting ovulation by administration of drospirenone and the use of drospirenone and ethinylestradiol for inhibiting ovulation.

BACKGROUND OF THE INVENTION

Oral contraceptives containing a combination of a gestagen and an estrogen component have been used since the 1960's. The earliest contraceptive preparations consisted of 21 tablets containing the combination of active agents and 7 tablets containing no active agent, and the amount of each active agent was the same in each tablet (the so-called one-phase preparations). Subsequently, preparations were developed that consisted of tablets containing different amounts and ratios of the active agents over the cycle of administration (the so-called multiple-phase preparations).

Contraceptive reliability is mainly provided by the gestagen component. The daily dosage should be at least the minimum of what is needed for the gestagen in question to inhibit ovulation effectively. The estrogen component acts to increase the ovulation inhibitory effect of gestagen and to ensure cycle stability. Since the introduction of oral contraceptives, the daily dosage of gestagen has been reduced through the development of new and more efficient gestagens than were present in the earlier contraceptive preparations. It has also been possible to reduce the daily dosage of estrogen.

6β,7β;15β,16β-dimethylene-3-oxo-17α-pregn-4-ene-21,17-carbolactone (drospirenone) is known from DE 26 52 761 in which its use as a diuretic compound is disclosed.

In DE 30 22 337, the gestagen-like activity of the compound and its consequent utility as a contraceptive agent is described at dosage levels of 0.5–50 mg of drospirenone per day. It is also noted that the mechanism of action of the compound is very similar to that of the natural corpus luteum hormone progesterone, and that it does not give rise to increased blood pressure for which reason it may be administrated to women who have or are at risk of developing increased blood pressure. It is further described that drospirenone may be administered together with ethinylestradiol in an amount of 0.03–0.05 mg per day.

DE 30 51 166 discloses the use of the drospirenone for the treatment of gynaecological irregularities and for contraception at a dosage level of 0.5–50 mg per day.

EP 398 460 discloses the use of drospirenone for the treatment of androgen-induced disorders, aldosterone-induced disorders and hormonal irregularities as well as for contraception at dosage levels of 0.5–50 mg, preferably 1–10 mg per day. Ethinylestradiol may be co-administered at a level of 0.02–0.04 mg per day.

U.S. Pat. No. 5,756,490 discloses pharmaceutical combination preparations comprising 23 or 24 dosage units containing a combination of a gestagen and an estrogen and 4–10 dosage units containing estrogen alone. Drospirenone is mentioned as a possible, but not preferred, gestagenic compound and ethinylestradiol is mentioned as a possible, but not preferred, estrogenic compound.

SUMMARY OF THE INVENTION

Accordingly, in a first aspect, the present invention relates to a pharmaceutical composition comprising, as a first active agent, 6β,7β;15β,16β-dimethylene-3-oxo-17α-pregn-4-ene-21,17-carbolactone (drospirenone) in an amount corresponding to a daily dosage, on administration of the composition, of from about 2 mg to about 4 mg, and, as a second active agent, 17α-ethinylestradiol (ethinylestradiol) in an amount corresponding to a daily dosage of from about 0.01 mg to about 0.05 mg, together with one or more pharmaceutically acceptable carriers or excipients.

Apart form the active substances themselves, it is envisaged that an ester or prodrug of drospirenone may be employed in the present composition, e.g. an oxyiminopregnane carbolactone as disclosed in WO 98/24801. Likewise, it is envisaged that esters or ethers of ethinylestradiol may be included in the composition.

In a further aspect, the invention relates to a method of inhibiting ovulation in a mammal, in particular a human, comprising administering, to said mammal, drospirenone in an amount in the range of from about 2 mg to about 4 mg of per day, together with ethinylestradiol in an amount of from about 0.01 mg to about 0.05 mg per day, said amounts being effective to inhibit ovulation in said mammal.

In a still further aspect, the invention relates to the use of drospirenone combined with ethinylestradiol for preparing a pharmaceutical preparation for the inhibition of ovulation in a mammal, in particular a human, the composition comprising an amount of drospirenone corresponding to a daily dosage, on administration of the composition, of from about 2 mg to about 4 mg, and comprising an amount of ethinylestradiol corresponding to a daily dosage, on administration of the composition, of from about 0.01 to about 0.05 mg.

BRIEF DESCRIPTION OF THE DRAWINGS

The invention is further described with reference to the drawings in which.

DETAILED DISCLOSURE OF THE INVENTION

Figure 1:
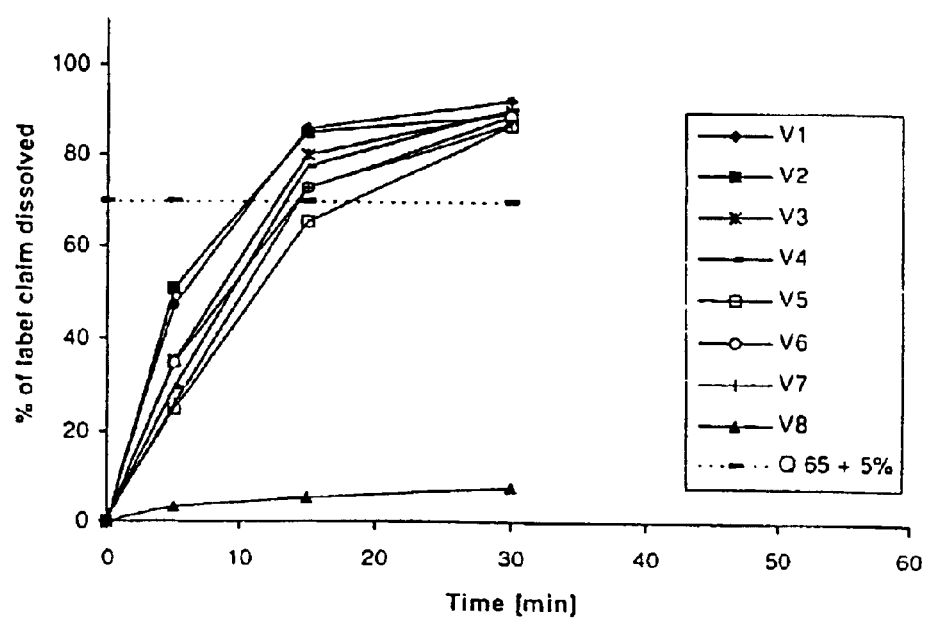
FIG. 1 is a graph showing the in vitro dissolution rate of drospirenone from tablet cores V1–V7 being batches containing micronized drospirenone, and V8 being a batch containing macrocrystalline drospirenone.

Drospirenone, which may be prepared substantially as described in, e.g., U.S. Pat. No. 4,129,564 or WO 98/06738, is a sparingly soluble substance in water and aqueous buffers at various pH values. Furthermore, drospirenone is rearranged to an inactive isomer under acid conditions and hydrolysed under alkaline conditions. To ensure good bioavailability of the compound, it is therefore advantageously provided in a form that promotes rapid dissolution thereof.

It has surprisingly been found that when drospirenone is provided in micronized form (so that particles of the active substance have a surface area of more than 10,000 $cm^2/g$, and the following particle size distribution as determined under the microscope: not more than 2% of the particles in a given batch have a diameter of more than 30 $\mu$m, and preferably $\leq$20% of the particles have a diameter of $\geq$10 $\mu$m and $\leq$30 $\mu$m) in a pharmaceutical composition, rapid dissolution of the active compound from the composition occurs in vitro ("rapid dissolution" is defined as the dissolution of at least 70% over about 30 minutes, in particular at least 80% over about 20 minutes, of drospirenone from a tablet preparation containing 3 mg of drospirenone in 900 ml of water at 37° C. determined by the USP XXIII Paddle Method using a USP dissolution test apparatus 2 at 50 rpm). Instead of providing the drospirenone in micronized form, it is possible to dissolve it in a suitable solvent, e.g. methanol or ethyl acetate, and spray it onto the surface of inert carrier particles followed by incorporation of the particles containing drospirenone on their surface in the composition.

Without wishing to be limited to any particular theory, it appears that the in vitro dissolution rate of drospirenone is connected to the dissolution rate in vivo resulting in rapid absorption of drospirenone in vivo on oral administration of the compound. This is an advantage because isomerization of the compound in the gastric environment and/or hydrolysis in the intestine is substantially reduced, leading to a high bioavailability of the compound.

With respect to ethinylestradiol which is also a sparingly soluble substance, though less sensitive to degradation than drospirenone under conditions prevailing in the gastrointestinal tract, it is also an advantage to provide it in micronized form or sprayed from a solution, e.g. in ethanol, onto the surface of inert carrier particles. This has the added advantage of facilitating a more homogenous distribution of the ethinylestradiol throughout the composition which might otherwise be difficult to obtain because ethinylestradiol is incorporated in extremely small amounts. When ethinylestradiol is provided in micronized form, it preferably has the following particle size distribution as determined under the microscope: 100% of the particles have a diameter of $\leq$15.0 $\mu$m, 99% of the particles have a diameter of $\leq$12.5 $\mu$m, 95% of the particles have a diameter of $\leq$10.0 $\mu$m, and 50% of the particles have a diameter of $\leq$3.0 $\mu$m. Furthermore, no particle is larger than 20 $\mu$m, and >10 particles have a diameter of $\geq$15 $\mu$m and $\leq$20 $\mu$m.

To obtain a more rapid rate of dissolution, it is preferred to include carriers or excipients which act to promote dissolution of both active substances. Examples of such carriers and excipients include substances that are readily soluble in water such as cellulose derivatives, carboxymethylcellulose, hydroxypropyl cellulose, hydroxypropylmethyl cellulose, gelled starch, gelatin or polyvinylpyrrolidone. In particular, it appears as though polyvinylpyrrolidone might be particularly helpful to promote dissolution.

The composition of the invention preferably comprises drospirenone in an amount corresponding to a daily dosage of from about 2.5 mg to about 3.5 mg, in particular about 3 mg. The amount of ethinylestradiol preferably corresponds to a daily dosage of from about 0.015 mg to about 0.04 mg, in particular from about 0.015 mg to about 0.03 mg. More particularly, the present composition comprises an amount of drospirenone corresponding to a daily dosage of from about 3.0 to about 3.5 mg and ethinylestradiol in an amount corresponding to from about 0.015 to about 0.03 mg.

Apart from its ability to inhibit ovulation, the composition of the invention has been found to possess pronounced anti-androgenic properties and may therefore be used in the prevention or treatment of androgen-induced disorders, in particular acne. Such use may be independent from or concomitant with the use as a contraceptive disclosed above. Furthermore, since drospirenone is an aldosterone antagonist, it has diuretic properties and is therefore suitable for counteracting the water-retentive properties of ethinylestradiol.

In a particular embodiment, the invention relates to a pharmaceutical preparation consisting of a number of separately packaged and individually removable daily dosage units placed in a packaging unit and intended for oral administration for a period of at least 21 consecutive days, wherein each of said daily dosage units comprises a combination of drospirenone in an amount of from about 2 mg to about 4 mg and ethinylestradiol in an amount from about 0.01 to about 0.05 mg.

In one embodiment, the preparation further comprises 7 or less said daily dosage units containing no active agent. Alternatively, it is possible to include, in the dosage regimen, a period of 7 days or less during which no dosage units are ingested. For compliance reasons, however, it may be preferred to include an appropriate number of blanks in the preparation, in which case the total number of daily dosage units in the preparation is at least 28. The inclusion of blanks, or the pill-free days, will then trigger withdrawal bleeding.

The preparation may be a one-phase composition, i.e. a preparation wherein the amounts of either active agent remains constant for the entire at least 21-day period, or the amounts of either or both active agents may be varied over the at least 21-day period to generate a multiple-phase preparation, e.g. a two- or three-phase preparation, substantially as disclosed in, e.g., EP 148 724. In case of multiple-phase preparation, it may be possible to include a natural estrogen such as estradiol, e.g. in an amount of from about 0.5 mg to about 4 mg per day, instead of ethinylestradiol.

In suitable embodiments of the present preparation, the number of daily dosage units comprising the combination of drospirenone and ethinylestradiol may be 21, 22, 23 or 24, and the number of daily dosage units containing no active agent may then be 7, 6, 5 or 4, as the case may be. In a further embodiment of the present preparation, the number of daily dosage units comprising the combination of drospirenone and ethinylestradiol is 28, or a multiple of 28 such as 2–4, in particular 2 or 3, times 28.

In an alternative embodiment, the invention relates to a contraceptive preparation consisting of a number of separately packaged and individually removable daily dosage units placed in a packaging unit and intended for oral administration for a period of at least 28 consecutive days, wherein at least 21 of said daily dosage units comprises a combination of drospirenone in an amount of from about 2 mg to about 4 mg and ethinylestradiol in an amount from about 0.01 to about 0.05 mg, and wherein 7 or less of said daily dosage units contain ethinylestradiol alone in an amount from about 0.01 to about 0.05 mg.

By including an appropriate number of dosage units comprising ethinylestradiol alone, high contraceptive reliability, low follicular development and satisfactory cycle control with little or no intermenstrual bleeding may be obtained.

In this case, too, the preparation may be one in which the amounts of either active agent remains constant for the entire at least 21-day period (i.e. a two-phase preparation), or the amounts of either or both active agents may be varied over the at least 21-day period to generate a multiple-phase preparation, e.g. a three- or four-phase preparation, substantially as disclosed in, e.g., EP 148 724. In case of multiple-phase preparation, it may be possible to include a natural estrogen such as estradiol, e.g. in an amount of from about 0.5 mg to about 4 mg per day, instead of ethinylestradiol.

In suitable embodiments of the present preparation, the number of daily dosage units comprising the combination of drospirenone and ethinylestradiol may be 21, 22, 23 or 24, and the number of daily dosage units containing ethinylestradiol alone may then be 7, 6, 5 or 4, as the case may be.

In one embodiment of the present method of inhibiting ovulation, the method comprises administering, to said mammal, on each day of at least 21 consecutive days, a daily dosage unit comprising a combination of drospirenone in an amount of from about 2 mg to about 4 mg and ethinylestradiol in an amount from about 0.01 to about 0.05 mg, followed by administering, on each day of 7 or less consecutive days, a daily dosage unit containing no active agent, or alternatively, administering no dosage units for 7 days or less.

In suitable embodiments of this method, the daily dosage units comprising the combination of drospirenone and ethinylestradiol may be administered for 21, 22, 23 or 24 consecutive days, and the daily dosage units containing no active agent may then be administered for 7, 6, 5 or 4 consecutive days, as appropriate. Furthermore, the daily dosage units comprising the combination of drospirenone and ethinylestradiol may be administered for 28 consecutive days. In a variant of this embodiment, the daily dosage units comprising the combination of drospirenone and ethinylestradiol are administered for 2–4, preferably 2 or 3, times 28 consecutive days, followed by administration of the daily dosage units comprising the combination of drospirenone and ethinylestradiol for 21, 22, 23 or 24 consecutive days and subsequently administration of the daily dosage units containing no active agent, or administration of no daily dosage units, for 7, 6, 5 or 4 consecutive days.

Alternatively, the present method comprises administering, on each day of at least 21 consecutive days, a daily dosage unit comprising a combination of drospirenone in an amount of from about 2 mg to about 4 mg and ethinylestradiol in an amount from about 0.01 to about 0.05 mg, followed by administering, on each day of 7 or less consecutive days, a daily dosage unit containing ethinylestradiol alone in an amount of from about 0.01 mg to about 0.05 mg.

In this alternative method, the daily dosage units comprising the combination of drospirenone and ethinylestradiol may suitably be administered for 21, 22, 23 or 24 consecutive days, and wherein the daily dosage units comprising ethinylestradiol alone may then be administered for 7, 6, 5 or 4 consecutive days, as appropriate. In a further embodiment of the method, the daily dosage units comprising the combination of drospirenone and ethinylestradiol are administered for 2–4, preferably 2 or 3, times 28 consecutive days, followed by administration of the daily-dosage units comprising the combination of drospirenone and ethinylestradiol for 21 consecutive days and subsequently administration of the daily dosage units comprising ethinylestradiol alone for 7 consecutive days.

For use according to the invention, the pharmaceutical preparation may suitably be in the form of a number of separately packaged and individually removable daily dosage units placed in a packaging unit and intended for oral administration for a period of at least 21 consecutive days, wherein each of said daily dosage units each comprises a combination of drospirenone in an amount of from about 2 mg to about 4 mg and ethinylestradiol in an amount from about 0.01 to about 0.05 mg.

As indicated above, the preparation may further comprise 7 or less daily dosage units containing no active agent (or may contain 7 or less empty "places", e.g. in the form of empty blisters in a blister pack, marking the days on which no daily dosage units are administered).

Alternatively, the pharmaceutical preparation may be in the form of a number of separately packaged and individually removable daily dosage units placed in a packaging unit and intended for oral administration for a period of at least 28 consecutive days, wherein at least 21 of said daily dosage units each comprises a combination of drospirenone in an amount of from about 2 mg to about 4 mg and ethinylestradiol in an amount of from about 0.01 to about 0.05 mg, said packaging unit further comprising 7 or less daily dosage units comprising ethinylestradiol alone in an amount of from about 0.01 mg to about 0.05 mg.

The composition of the invention may be formulated in any manner known in the pharmaceutical art. In particular, as indicated above, the composition may be formulated by a method comprising providing drospirenone and, if desired, ethinylestradiol in micronized form in said unit dosage form, or sprayed from a solution onto particles of an inert carrier in admixture with one or more pharmaceutically acceptable excipients that promote dissolution of the drospirenone and ethinylestradiol so as to promote rapid dissolution of drospirenone and preferably ethinylestradiol on oral administration. Examples of suitable excipients include fillers, e.g. sugars such as lactose, glucose or sucrose, sugar alcohols such as mannitol, sorbitol or xylitol, starch such as wheat, corn or potato starch, modified starch or sodium starch glycolate, lubricants such as talc, magnesium stearate, calcium stearate, colloidal silica or stearic acid, and binders such as polyvinylpyrrolidone, cellulose derivatives, carboxymethyl cellulose, hydroxypropyl cellulose, hydroxypropylmethyl cellulose, methyl cellulose or gelatin, for making oral dosage forms such as tablets, pills or capsules.

Tablets may conveniently be coated with a suitable film-forming agent, e.g. hydroxypropylmethyl cellulose, hydroxypropyl cellulose or ethyl cellulose, to which a suitable excipient may optionally be added, e.g. a softener such as glycerol, propylene glycol, diethylphthalate or glycerol triacetate, filler such as sucrose, sorbitol, xylitol, glucose or lactose, a colorant such as titanium hydroxide, etc.

The present composition may also be formulated in liquid form, e.g. as a solution, suspension or emulsion, together with conventional diluents or excipients in a manner known per se in the pharmaceutical art.

A packaging unit comprising the daily dosage units described above may be prepared in a manner analogous to that of making other oral contraceptives. This may for instance be a conventional blister pack or any other form known for this purpose, for instance a pack comprising the appropriate number of dosage units (in this case at least 21, or for particular applications, 28 or a multiple of 28) in a sealed blister pack with a cardboard, paperboard, foil or plastic backing and enclosed in a suitable cover. Each blister container may conveniently be numbered or otherwise marked, e.g. starting with the first of the at least 21 dosage units that contain the combination of drospirenone and ethinylestradiol, optionally followed by 7 or less empty blisters or by the 7 or less dosage units that contain no active agent or that only contain ethinylestradiol (although the numbering may also start with the first of the 7 or less dosage units that only contain ethinylestradiol).

It is also envisaged that the present composition may be in the form of a parenteral formulation such as a subcutaneous implant or transdermal formulation. For making implants, the active agents may suitably be formulated together with one or more polymers that are gradually eroded or degraded when in use, e.g. silicone polymers, ethylene vinylacetate, polyethylene or polypropylene.

Where transdermal formulations are concerned, they may be prepared in the form of matrices or membranes or as fluid or viscous formulations in oil or hydrogels. For transdermal patches, an adhesive which is compatible with the skin should be included, such as polyacrylate, a silicone adhesive or polyisobutylene, as well as a foil made of, e.g. polyethylene, polypropylene, ethylene vinylacetate, polyvinylchloride, polyvinylidene chloride or polyester, and a removable protective foil made from, e.g., polyester or paper coated with silicone or a fluoropolymer. For the preparation of transdermal solutions or gels, water or organic solvents or mixtures thereof may be used. Transdermal gels may furthermore contain one or more suitable gelling agents or thickeners such as silicone, tragacanth, starch or starch derivatives, cellulose or cellulose derivatives or polacrylic acids or derivatives thereof. Transdermal formulations may also suitably contain one or more substances that enhance absorption though the skin, such as bile salts or derivatives thereof and/or phospholipids. Suitable transdermal formulations may, for instance, be made in a manner analogous to that described in WO 94/04157 for 3-ketodesogestrel. Alternatively, transdermal formulations may be prepared according to a method disclosed in, e.g., B W Barry, "Dermatological Formulations, Percutaneous Absorption", Marcel Dekker Inc., New York—Basel, 1983, or Y W Chien, "Transdermal Controlled Systemic Medications", Marcel Dekker Inc., New York—Basel, 1987.

The present invention is further described in the following examples which are not in any way intended to limit the scope of the invention as claimed.

EXPERIMENTAL

EXAMPLE 1

Preparation of Tablets Containing Drospirenone and Ethinylestradiol

Tablet cores of the following composition

| | |
|---|---|
| micronized drospirenone | 3.00 mg |
| micronized ethinylestradiol | 0.03 mg |
| lactose monohydrate | 48.17 mg |
| corn starch | 14.40 mg |
| modified starch | 9.60 mg |
| polyvinylpyrrolidone 25,000 | 4.00 mg |
| magnesium stearate | 0.80 mg | were prepared by charging a fluidized bed granulator with 31.68 kg corn starch, 21.12 kg modified starch, 6.60 micronized drospirenone, 0.066 kg micronized ethinylestradiol and 105.974 kg lactose monohydrate and activating the fluidized bed. An aqueous solution of 8.80 kg polyvinylpyrrolidone 25,000 in 46.20 kg purified water was sprayed continuously onto the fluidized bed while drying by heating the air stream of the fluidized bed. At the end of the process 1.76 kg magnesium stearate was sucked into the granulator and mixed with the granules by maintaining the fluidized bed. The resulting granulate was pressed into tablet cores by compression using a rotary tablet press.

2.22464 kg of hydroxypropylmethylcellulose and 0.44528 macrogol 6000 were dissolved in 14.67 kg purified water. 0.44528 kg talc, 1.22430 kg titanium dioxide and 0.06050 kg ferric oxide pigment were suspended in 10.26 kg purified water with stirring and homogenized. The solution and suspension were combined and used to coat the tablet cores by continuous application of the coating suspension in a coater.

EXAMPLE 2

Dissolution of Drospirenone from Tablets

The rate of dissolution of drospirenone from the tablets prepared in Example 1 is determined by the USP XXIII Paddle Method using a USP Dissolution Test Apparatus 2 including 6 covered glass vessels and 6 paddles. Tablets are placed in 900 ml water at a temperature of 37° C. (±0.5° C.) and stirred at 50 rpm.

Figure 2:
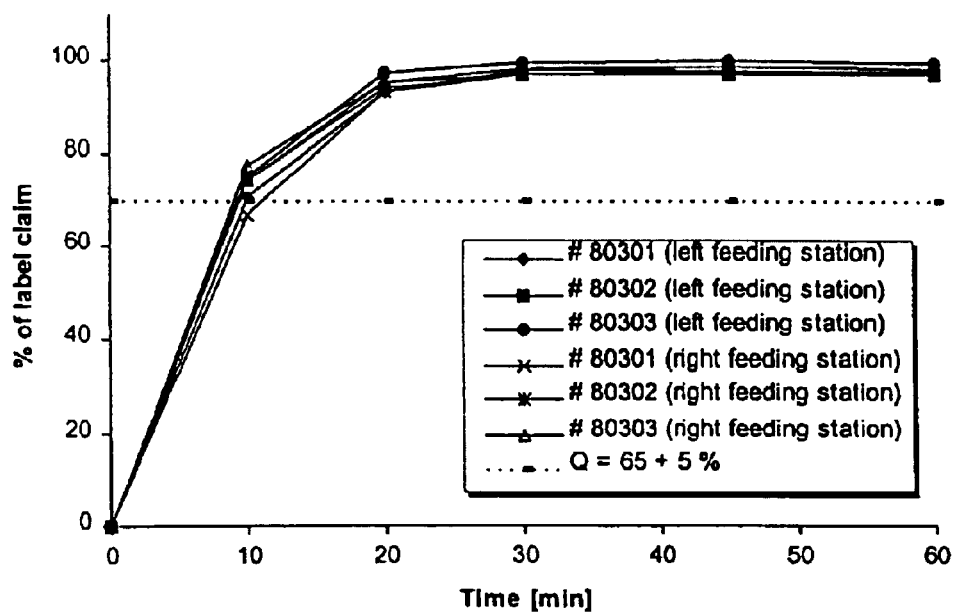
FIG. 2 is a graph showing the in vitro dissolution rate of drospirenone from tablet cores, different lines representing different test batches.
Figure 3:
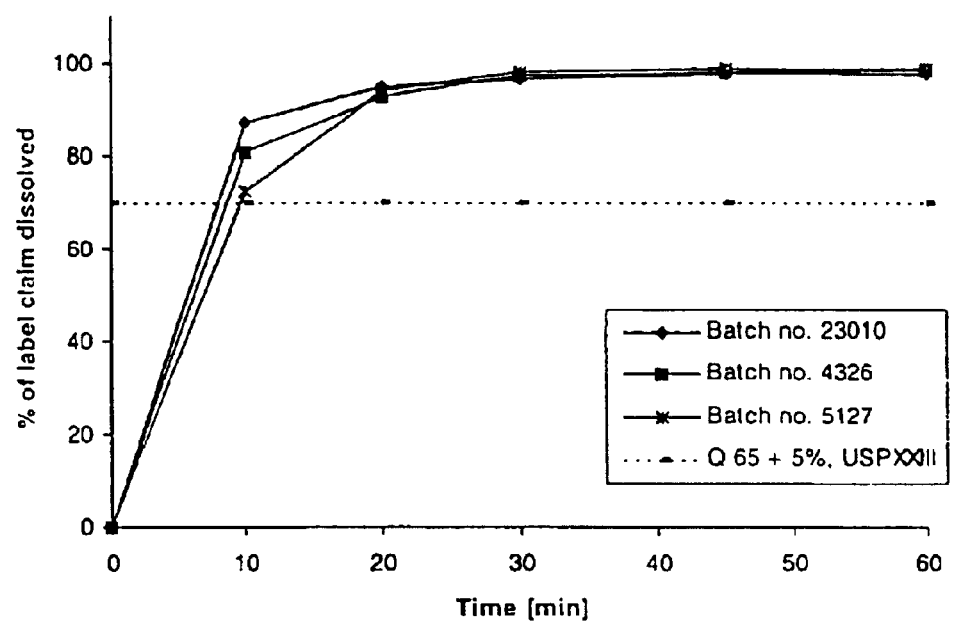
FIG. 3 is a graph showing the in vitro dissolution rate of drospirenone from film-coated tablets, different lines representing different test batches.

The results appear from FIGS. 1, 2 and 3. From FIG. 1, it appears that the batch numbered V8 containing macrocrystalline drospirenone (but otherwise identical to the tablets prepared in Example 1) exhibits an extremely slow dissolution rate of drospirenone, whereas all batches containing micronized drospirenone exhibit a dissolution rate of more than 70% within 30 minutes.

FIG. 2 and FIG. 3 show the results of dissolution of drospirenone from tablet cores and film-coated tablets, respectively. In both cases more than 70% of the active agent is dissolved within 30 minutes. Thus, the film coating does not significantly influence the rate of dissolution.

EXAMPLE 3

Dissolution Rate of Ethinylestradiol from Tablets in Vitro

Figure 4:
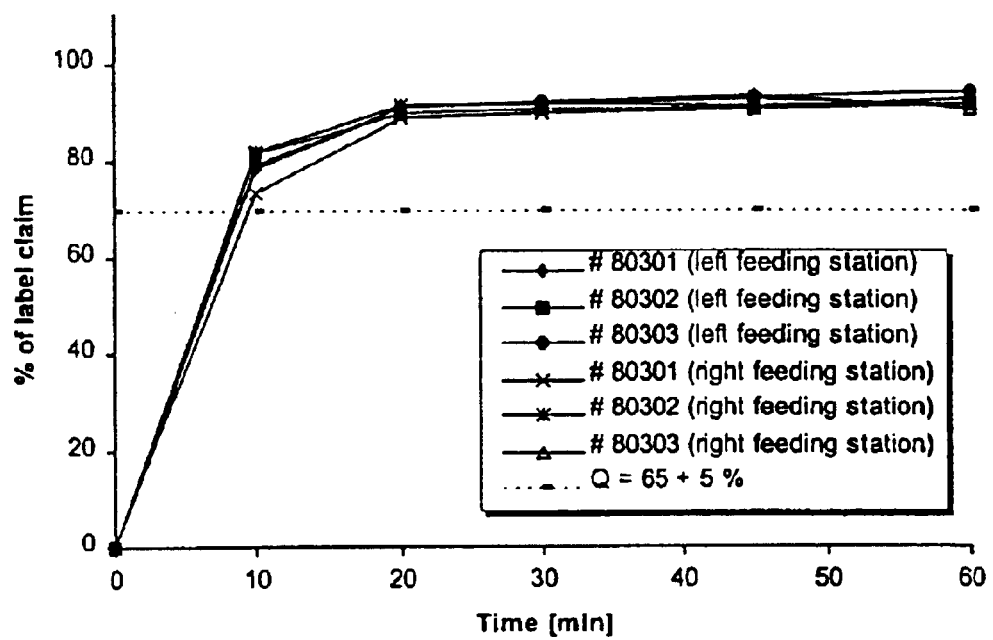
FIG. 4 is a graph showing the in vitro dissolution rate of ethinylestradiol from tablet cores, different lines representing different test batches.
Figure 5:
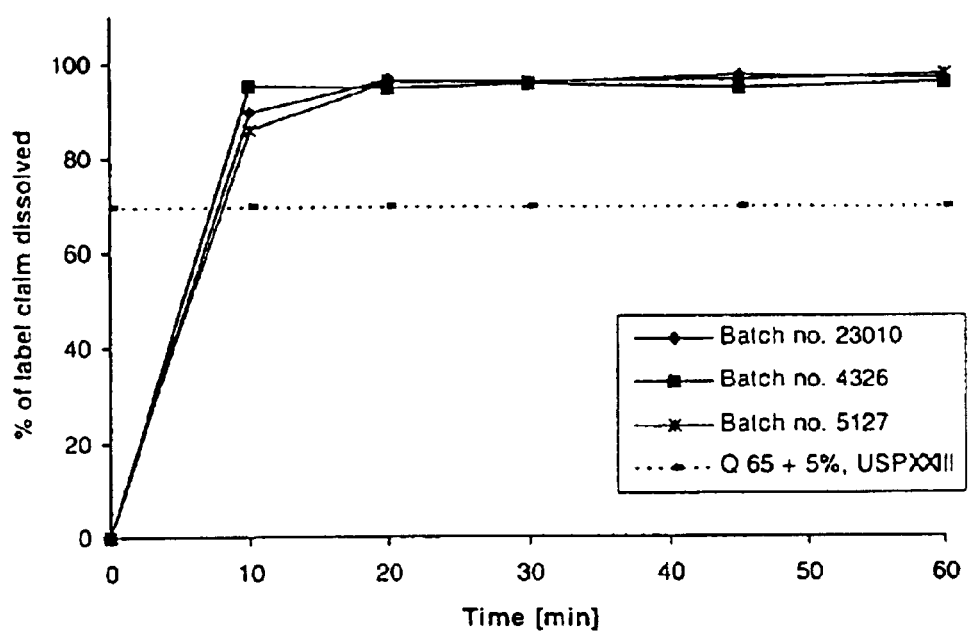
FIG. 5 is a graph showing the in vitro dissolution rate of ethinylestradiol from film-coated tablets, different lines representing different test batches.

The rate of dissolution of ethinylestradiol from tablets prepared as described in Example 1 is determined according to the USP Paddle Method as described in Example 2 for drospirenone. The results appear from FIGS. 4 and 5 showing the dissolution rates from tablet cores and film-coated tablets, respectively. In both cases, more than 70% of the active agent is dissolved within 30 minutes. Thus, the film coating does not significantly influence the rate of dissolution.

EXAMPLE 4

Bioavailability of Drospirenone and Ethinylestradiol from Tablets Containing 3 mg of Drospirenone and 0.03 mg Ethinylestradiol 42 healthy women between 18 and 35 years of age were included in an open-label crossover study after their informed consent had been obtained. The aim of the study was to investigate the relative bioavailability of drospirenone and ethinylestradiol from a tablet formulation containing 3 mg drospirenone and 0.03 mg ethinylestradiol with reference to an oral suspension containing 6 mg of drospirenone and 0.06 mg ethinylestradiol per vial.

The bioavailability was determined using serum concentrations of each active agent as parameters. Compared to the oral suspension, the relative bioavailability of drospirenone and ethinylestradiol from the tablets is 107% and 117%, respectively. It was therefore concluded that both drospirenone and ethinylestradiol are completely released from the tablets in vivo.

The absolute bioavailability of drospirenone was determined in two studies to be 76%±13% after oral administration of 2 mg drospirenone to 8 young healthy women and 85%±24% after oral administration of a microcrystalline suspension containing 3.13 mg drospirenone to 6 postmenopausal women.

The oral bioavailability of ethinylestradiol was determined in several studies, and mean values of from 36% to 59% were reported in the literature, indicating a first-pass effect.

EXAMPLE 5

Contraceptive Efficacy of Formulations Containing Drospirenone and Ethinylestradiol An open-label, randomized trial with 52 female volunteers aged 20–35 years whose informed consent is obtained includes 1 pre-treatment cycle, 3 treatment cycles with two different tablets containing 2 mg and 3 mg drospirenone, respectively, but otherwise corresponding to the tablets prepared in Example 1, and a follow-up phase. A wash-out phase of 1 month precedes the treatment.

At defined time points, selected central and peripheral parameters are investigated: LH, FSH, $17\alpha$-estradiol, progesterone, cervical score, "spinnbarkeit", fern phenomenon. Ovarian function is checked by ultrasound. In addition, SHBG, CBG, prolactine, total testosterone, androstenedione, DHEA-S and selected metabolic parameters (serum glucose, triglycerides, cholesterol, HDL, LDL) are examined. Blood pressure, heart rate, body weight and cycle control are documented.

The results of the study show that both LH and FSH are clearly suppressed with both trial preparations. Accordingly, the secretion of estradiol and progesterone are greatly reduced over all three treatment cycles with the exception of 3 volunteers receiving the 2 mg drospirenone preparation. This result is, in principle, confirmed by the accompanying ultrasound examinations. Follicular ripening occurs in several cases with both trial preparations. Although three ovulations are diagnosed with the preparation containing 2 mg drospirenone (one of which was described as "equivocal" and the other as a "tablet-taking error"), no differences are demonstrable statistically (p>0.05) between the two trial preparations as regards the hormones LH, FSH, estradiol and progesterone, and the parameter "ovulation during the treatment cycles". In keeping with the hormones, cervical function is greatly limited and the "spinnbarkeit" and crystallisability of the cervical mucus is greatly reduced with both trial preparations. Prolactin increases minimally and SHBG and CBG distinctly with both preparations. Triglycerides and HDL levels increases with both trial preparations, while LDL levels decrease. Total cholesterol is largely unchanged in both treatment groups. Oral glucose tolerance remains virtually unchanged or is slightly decreased. Testosterone, androstenedione and DHEA-S decrease minimally.

The subjective and objective tolerance is good with both treatments. This is also the case for cycle control with the exception of the first cycle with 2 mg drospirenone. Blood pressure, heart rate and body weight remain constant in the majority of cases or show a slight tendency to decrease.

After three months treatment it is concluded:

The two trial preparations are equally good as regards the subjective and objective tolerance.

No negative metabolic effects are observed with either preparation. HDL is influenced positively in the sense of an increase.

The results confirm the results of earlier studies that the 2 mg drospirenone preparation is in the region of ovulation inhibition, whereas the 3 mg drospirenone preparation has a demonstrable ovulation-inhibiting effect in all cases examined.

The preceding examples can be repeated with similar success by substituting the generically or specifically described reactants and/or operating conditions of this invention for those used in the preceding examples.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents and publications, cited above and below, and of corresponding U.S. application Ser. No. 09/386,274, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition comprising from about 2 mg to about 4 mg of micronized drospirenone particles, about 0.01 mg to about 0.05 mg of $17\alpha$-ethinylestradiol, and one or more pharmaceutically acceptable carriers, the composition being in an oral dose form exposed to the gastric environment upon dissolution, and the composition being effective for oral contraception in a human female.

2. A composition according to claim 1, wherein the amount of drospirenone is from about 2.5 mg to about 3.5 mg.

3. A composition according to claim 1 wherein the ethinylestradiol is in micronized form or sprayed from a solution onto particles of an inert carrier.

4. A composition according to claim 1, wherein the amount of ethinylestradiol is from about 0.015 mg to about 0.04 mg.

5. A composition according to claim 1, wherein the amount of drospirenone is from about 3.0 to about 3.5 mg and the amount of ethinylestradiol is from about 0.015 to about 0.03 mg.

6. A composition according to claim 1, wherein the pharmaceutically acceptable carrier promotes rapid dissolution of the drospirenone and $17\alpha$-ethinylestradiol, the dissolution being determined by applying the USP XXIII Paddle Method using a USP dissolution test apparatus 2 at a stirring rate of 50 rpm, including 6 covered glass vessels and 6 paddles, the dissolution media being 900 ml of water at 37° C. (±0.5° C.), and wherein rapid dissolution means that at least 70% of the drospirenone, when provided as a tablet containing 3 mg of drospirenone, is dissolved within 30 minutes.

7. A composition according to claim 6, wherein at least 80% of the drospirenone is dissolved within 20 minutes.

8. A pharmaceutical kit comprising a number of separately packaged, individually removable, daily dosage units, in an oral dose form exposed to the gastric environment upon dissolution, placed in a packaging unit and intended for oral administration for a period of 21 consecutive days, wherein said daily dosage units each comprise a combination of micronized drospirenone particles in an amount of from about 2 mg to about 4 mg and 17α-ethinylestradiol in an amount from about 0.01 to about 0.05 mg, and wherein said daily dosage units comprising drospirenone are effective for oral contraception in a human female.

9. A kit according to claim 8, which additionally comprises 7 daily dosage units containing no active agent intended for oral administration subsequent to the period of 21 consecutive days, the total number of daily dosage units being at least 28.

10. A pharmaceutical kit comprising a number of separately packaged, individually removable, daily dosage units, in an oral dose form exposed to the gastric environment upon dissolution, placed in a packaging unit and intended for oral administration for a period of 22, 23 or 24 consecutive days, wherein said daily dosage units each comprise a combination of micronized drospirenone particles in an amount of from about 2 mg to about 4 mg and 17α-ethinylestradiol in an amount from about 0.01 to about 0.05 mg, and a number of daily dosage units containing no active agent which is 6, 5 or 4, and wherein said daily dosage units comprising drospirenone are effective for oral contraception in a human female.

11. A pharmaceutical kit comprising a number of separately packaged, individually removable, daily dosage units, in an oral dose form exposed to the gastric environment upon dissolution, placed in a packaging unit and intended for oral administration for a period of 28, or a multiple of 28, consecutive days, wherein said daily dosage units each comprise a combination of micronized drospirenone particles in an amount of from about 2 mg to about 4 mg and 17α-ethinylestradiol in an amount from about 0.01 to about 0.05 mg, and wherein said daily dosage units comprising drospirenone are effective for oral contraception in a human female.

12. A kit according to claim 11, which additionally comprises a number of daily dosage units comprising the combination of drospirenone and ethinylestradiol which is a multiple of 21, 22, 23 or 24, and comprises a number of daily dosage units containing no active agent which is a multiple of 7, 6, 5 or 4.

13. A kit according to claim 8, wherein the 21 daily dosage units comprise drospirenone in an amount of from about 2.5 mg to about 3.5 mg and 17α-ethinylestradiol in an amount of from about 0.015 mg to about 0.04 mg.

14. A kit according to claim 8, wherein the daily dosage units comprise drospirenone in an amount of from about 3.0 to about 3.5 mg and 17α-ethinylestradiol in an amount of from about 0.015 to about 0.03 mg.

15. A pharmaceutical kit comprising a number of separately packaged, individually removable, daily dosage units, in an oral dose form exposed to the gastric environment upon dissolution, placed in a packaging unit and intended for oral administration for a period of at least 28 consecutive days, wherein at least 21 of said daily dosage units comprise a combination of micronized drospirenone particles in an amount of from about 2 mg to about 4 mg and 17α-ethinylestradiol in an amount from about 0.01 to about 0.05 mg, wherein at least 1 but no more than 7 of said daily dosage units contain 17α-ethinylestradiol in an amount from about 0.01 to about 0.05 mg and contain no drospirenone, and wherein said daily dosage units comprising drospirenone are effective for oral contraception in a human female.

16. A kit according to claim 13, wherein the number of daily dosage units comprising the combination of drospirenone and ethinylestradiol is 21, 22, 23 or 24, and wherein the number of daily dosage units comprising ethinylestradiol without drospirenone is 7, 6, 5 or 4.

17. A kit according to claim 15, wherein the at least 21 daily dosage units comprise drospirenone in an amount of from about 2.5 mg to about 3.5 mg and 17α-ethinylestradiol in an amount of from about 0.015 mg to about 0.04 mg.

18. A kit according to claim 15, wherein the at least 21 daily dosage units comprise drospirenone in an amount of from about 3.0 to about 3.5 mg and 17α-ethinylestradiol in an amount of from about 0.015 to about 0.03 mg.

19. The composition of claim 1, wherein the drospirenone is in the form of a prodrug of the compound.

20. The composition of claim 1, wherein the 17α-ethinylestradiol is in the form of an ester or ether of the compound.

21. The composition of claim 1, wherein the drospirenone is provided together with a carrier which is of carboxymethylcellulose, hydroxypropyl cellulose, hydroxypropylmethyl cellulose, gelled starch, gelatin or polyvinylpyrrolidone.

22. The kit of claim 8, wherein the drospirenone is provided together with a carrier which is of carboxymethylcellulose, hydroxypropyl cellulose, hydroxypropylmethyl cellulose, gelled starch, gelatin or polyvinylpyrrolidone.

23. The kit of claim 15, wherein the drospirenone is provided together with a carrier which is of carboxymethylcellulose, hydroxypropyl cellulose, hydroxypropylmethyl cellulose, gelled starch, gelatin or polyvinylpyrrolidone.

24. The kit of claim 8, wherein both the drospirenone and 17α-ethinylestradiol are micronized.

25. The kit of claim 15, wherein both the drospirenone and 17α-ethinylestradiol are micronized.

26. The composition of claim 19, wherein the prodrug is an ester of drospirenone.

27. A pharmaceutical composition comprising:
   from about 2 mg to about 4 mg of drospirenone particles, wherein the drospirenone has a surface area of more than 10 000 cm$^2$/g,
   about 0.01 to about 0.05 mg of 17α-ethinylestradiol, and
   one or more pharmaceutically acceptable carriers,
   the composition being in an oral dose form exposed to the gastric environment upon dissolution, and the composition being effective for oral contraception in a human female.

28. A pharmaceutical composition comprising:
   from about 2 mg to about 4 mg of drospirenone particles, wherein the drospirenone is in a form, which when provided in a tablet containing 3 mg of drospirenone, has a dissolution such that at least 70% of said drospirenone is dissolved in 900 ml of water at 37° C. (±0.5° C.) within 30 minutes, as determined by USP XXIII Paddle Method using a USP dissolution test apparatus 2 at a stirring rate of 50 rpm, including 6 covered glass vessels and 6 paddles,
   about 0.01 mg to about 0.05 mg of 17α-ethinylestradiol, and
   one or more pharmaceutically acceptable carriers,
   the composition being in an oral dose form exposed to the gastric environment upon dissolution, and the composition being effective for oral contraception in a human female.

29. A pharmaceutical kit comprising a number of separately packaged, individually removable, daily dosage units, in an oral dose form exposed to the gastric environment upon dissolution, placed in a packaging unit and intended for oral administration for a period of 21 consecutive days, wherein said daily dosage units each comprise a combination of drospirenone particles in an amount of from about 2 mg to about 4 mg, wherein the drospirenone has a surface area of more than 10 000 cm²/g, and 17α-ethinylestradiol in an amount from about 0.01 to about 0.05 mg, and wherein said daily dosage units comprising drospirenone are effective for oral contraception in a human female.

30. A pharmaceutical kit comprising a number of separately packaged, individually removable, daily dosage units, in an oral dose form exposed to the gastric environment upon dissolution, in a packaging unit and intended for oral administration for a period of 21 consecutive days, wherein said daily dosage units each comprise a combination of:

drospirenone particles in an amount of from about 2 mg to about 4 mg, wherein the drospirenone is in a form, which when provided in a tablet containing 3 mg of drospirenone, has a dissolution such that at least 70% of said drospirenone is dissolved in 900 ml of water at 37° C. (±0.5° C.) within 30 minutes, as determined by USP XXIII Paddle Method using a USP dissolution test apparatus 2 at a stirring rate of 50 rpm, including 6 covered glass vessels and 6 paddles, and 17α-ethinylestradiol in an amount from about 0.01 to about 0.05 mg, and wherein said daily dosage units comprising drospirenone are effective for oral contraception in a human female.

31. A pharmaceutical kit comprising a number of separately packaged, individually removable, daily dosage units, in an oral dose form exposed to the gastric environment upon dissolution, in a packaging unit and intended for oral administration for a period of at least 28 consecutive days, wherein at least 21 of said daily dosage units comprise a combination of:

drospirenone particles in an amount of from about 2 mg to about 4 mg, wherein the drospirenone has a surface area of more than 10 000 cm²/g, and 17α-ethinylestradiol in an amount from about 0.01 to about 0.05 mg, and wherein at least 1 but no more than 7 of said daily dosage units contain 17α-ethinylestradiol in an amount from about 0.01 to about 0.05 mg and contain no drospirenone, and wherein said daily dosage units comprising drospirenone are effective for oral contraception in a human female.

32. A pharmaceutical kit comprising a number of separately packaged, individually removable, daily dosage units, in an oral dose form exposed to the gastric environment upon dissolution, in a packaging unit and intended for oral administration for a period of at least 28 consecutive days, wherein at least 21 of said daily dosage units comprise a combination of drospirenone particles in an amount of from about 2 mg to about 4 mg, wherein the drospirenone is in a form, which when provided in a tablet containing 3 mg of drospirenone, has a dissolution such that at least 70% of said drospirenone is dissolved in 900 ml of water at 37° C. (±0.5° C.) within 30 minutes, as determined by USP XXIII Paddle Method using a USP dissolution test apparatus 2 at a stirring rate of 50 rpm, including 6 covered glass vessels and 6 paddles, and 17α-ethinylestradiol in an amount from about 0.01 to about 0.05 mg, and wherein at least 1 but no more than 7 of said daily dosage units contain 17α-ethinylestradiol in an amount from about 0.01 to about 0.05 mg and contain no drospirenone, and wherein said daily dosage units comprising drospirenone are effective for oral contraception in a human female.

33. A composition or kit of claim 28, 30 or 32, wherein at least 80% of said drospirenone is dissolved within 20 minutes by the stated test.

34. A composition or kit according to claim 27, 28, 29, 30, 31, or 32, wherein the 17α-ethinylestradiol is in micronized form.

35. A composition or kit according to claim 27, 28, 29, 30, 31 or 32, wherein the 17α-ethinylestradiol is sprayed from a solution onto particles of an inert carrier.

36. A composition or kit according to claim 27, 28, 29, 30, 31 or 32, wherein the amount of drospirenone is from 2.5 to 3.5 mg.

37. A composition or kit according to claim 27, 28, 29, 30, 31 or 32, wherein the amount of 17α-ethinylestradiol is from 0.015 to 0.04 mg.

38. A composition or kit according to claim 27, 28, 29, 30, 31 or 32 comprising a carrier effective to promote dissolution of drospirenone and ethinylestradiol.

39. A composition or kit according to claim 38 wherein said carrier is polyvinylpyrrolidone.

40. A pharmaceutical kit comprising a number of separately packaged, individually removable, daily dosage units, in an oral dose form exposed to the gastric environment upon dissolution, in a packaging unit, including active daily dosage units which comprise a combination of micronized drospirenone particles in an amount of from about 2 mg to about 4 mg and 17α-ethinylestradiol in an amount from about 0.01 to about 0.05 mg, wherein the kit is adapted for administering active daily dosage units for multiple cycles of 28 consecutive days each, followed by administering the active daily dosage units for 21, 22, 23 or 24 consecutive days and subsequently administering daily dosage units containing no active agent, or administering no daily dosage units, for 7, 6, 5 or 4 consecutive days, and wherein said daily dosage units comprising drospirenone are effective for oral contraception in a human female.

41. A pharmaceutical kit comprising a number of separately packaged, individually removable, daily dosage units, in an oral dose form exposed to the gastric environment upon dissolution, in a packaging unit, including active daily dosage units which comprise a combination of:

drospirenone particles in an amount of from about 2 mg to about 4 mg, wherein the drospirenone is in a form, which when provided in a tablet containing 3 mg of drospirenone, has a dissolution such that at least 70% of said drospirenone is dissolved in 900 ml of water at 37° C. (±0.5° C.) within 30 minutes, as determined by USP XXIII Paddle Method using a USP dissolution test apparatus 2 at a stirring rate of 50 rpm, including 6 covered glass vessels and 6 paddles, and 17α-ethinylestradiol in an amount from about 0.01 to about 0.05 mg, wherein the kit is adapted for administering active daily dosage units for multiple cycles of 28 consecutive days each, followed by administering active daily dosage units for 21, 22, 23 or 24 consecutive days and subsequently administering daily dosage units containing no active agent, or administering no daily dosage units, for 7, 6, 5 or 4 consecutive days, and wherein said daily dosage units comprising drospirenone are effective for oral contraception in a human female.

42. A pharmaceutical kit comprising a number of separately packaged, individually removable, daily dosage units, in an oral dose form exposed to the gastric environment upon dissolution, in a packaging unit, including active daily dosage units which comprise a combination of:

drospirenone particles in an amount of from about 2 mg to about 4 mg, wherein the drospirenone has a surface area of more than 10 000 $cm^2/g$, and 17α-ethinylestradiol in an amount from about 0.01 to about 0.05 mg, wherein the kit is adapted for administering active daily dosage units for multiple cycles of 28 consecutive days each, followed by administering active daily dosage units for 21, 22, 23 or 24 consecutive days and subsequently administering daily dosage units containing no active agent, or administering no daily dosage units, for 7, 6, 5 or 4 consecutive days, and wherein said daily dosage units comprising drospirenone are effective for oral contraception in a human female.

43. The kit according to claim 40, 41 or 42, wherein the multiple cycles of 28 consecutive days each is 2 to 4 such cycles.

44. A composition or kit according to claim 27, 28, 29, 30, 31, 32, 40, 41, 42 or 43 wherein the amount of drospirenone is from about 3.0 to about 3.5 mg and the amount of 17α-ethinylestradiol is from about 0.015 to about 0.03 mg.

45. A composition or kit according to claim 1, 27, 28, 29, 30, 31, 32, 40, 41, 42 or 43, wherein the amount of drospirenone is from 2.5 mg to 3.5 mg, and the amount of 17α-ethinylestradiol is from 0.015 mg to 0.04 mg.

46. A composition or kit according to claim 1, 8, 15, 27, 28, 29, 30, 31, 32, 40, 41, 42 or 43 wherein the 17α-ethinylestradiol is provided in an amount of from about 0.01 to about 0.04 mg and the drospirenone is provided in a form whereby the drospirenone is exposed to the gastric environment upon dissolution.

47. A composition according to claim 1, 27 or 28, wherein the composition is provided in a tablet, pill or capsule oral dosage form.

48. A kit according to claim 8, 15, 29, 30, 31, 32, 40, 41, 42 or 43 wherein the daily dosage units are provided in a tablet, pill or capsule oral dosage form.

49. A pharmaceutical composition comprising about 3 mg of micronized drospirenone particles, about 0.03 mg of micronized 17α-ethinylestradiol, and one or more pharmaceutically acceptable carriers, the composition being in a tablet, capsule or pill oral dose exposed to the gastric environment upon dissolution, and the composition being effective for oral contraception in a human female.

50. A pharmaceutical kit comprising a number of separately packaged, individually removable, daily dosage units, in an oral dose form exposed to the gastric environment upon dissolution, placed in a packaging unit and intended for oral administration for a period of 28 consecutive days, wherein 21 of said daily dosage units comprise a combination of micronized drospirenone particles in an amount of about 3 mg and micronized 17α-ethinylestradiol in an amount of about 0.03 mg, and wherein 7 of said daily dosage units contain no drospirenone or 17α-ethinylestradiol, and wherein said daily dosage units comprising drospirenone are effective for oral contraception in a human female.

51. The composition of claim 19, wherein the prodrug is an ester of drospirenone.

52. A kit according to claim 11, which additionally comprises daily dosage units comprising the combination of drospirenone and ethinylestradiol for 21, 22, 23 or 24 consecutive days and subsequent daily dosage units containing no active agent for 7, 6, 5 or 4 consecutive days.

* * * * *